United States Patent [19]

Akiyama

[11] 3,960,786
[45] June 1, 1976

[54] PROCESS FOR PREPARING GRANULAR POROUS SILICONE RUBBERS

[76] Inventor: Taichiro Akiyama, 19-23, Shimoochiai 2-Chome, Shinjuku, Tokyo, Japan

[22] Filed: May 30, 1974

[21] Appl. No.: 474,850

[30] Foreign Application Priority Data
June 6, 1973 Japan.............................. 48-62890

[52] U.S. Cl............................ 260/2.5 S; 260/2.5 L; 260/46.5 R; 260/825
[51] Int. Cl.² .......................................... C08J 09/00
[58] Field of Search....................... 260/2.5 S, 2.5 L

[56] References Cited
UNITED STATES PATENTS

| | | | |
|---|---|---|---|
| 2,833,732 | 5/1958 | Weyer............................. | 260/2.5 S |
| 2,956,032 | 10/1960 | Joyce............................... | 260/2.5 S |
| 3,024,210 | 3/1962 | Weyer............................. | 260/2.5 S |
| 3,070,555 | 12/1962 | Bruner............................ | 260/2.5 S |
| 3,127,363 | 3/1964 | Nitzsche......................... | 260/2.5 S |
| 3,271,332 | 9/1966 | Bond............................... | 260/2.5 S |
| 3,338,847 | 8/1967 | Nitzsche......................... | 260/2.5 S |
| 3,428,580 | 2/1969 | Nitzsche......................... | 260/2.5 S |
| 3,677,981 | 7/1972 | Wada.............................. | 260/2.5 S |
| 3,791,998 | 2/1974 | Bruns.............................. | 260/2.5 S |

*Primary Examiner*—Paul Lieberman
*Attorney, Agent, or Firm*—Ladas, Parry, Von Gehr, Goldsmith & Deschamps

[57] ABSTRACT

Granular porous silicone rubbers suitable to form articles to be embedded in human bodies or to be used to make up lost portions thereof are prepared by forming a composition containing a siloxnediole composition expressed by a formula

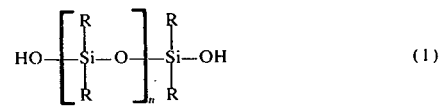

where R respectively represents a methyl radical, a phenyl radical or a vinyl radical and n is an integer of from 500 to 5,000, at least 0.5 % by weight based on the weight of the compound of formula (1) of a siloxanediol hydride compound expressed by a formula

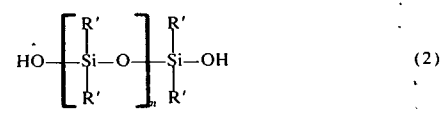

where R' respectively represents a hydrogen radical or a methyl radical but at least one of R' radicals is a hydrogen radical, and n is an integer of from 2 to 1,000, a vulcanization catalyst and an emulsifying agent. The composition is then dispersed in water and the resulting emulsion is vulcanized while it is stirred thereby forming the granules of porous silicones.

6 Claims, No Drawings

PROCESS FOR PREPARING GRANULAR POROUS SILICONE RUBBERS

BACKGROUND OF THE INVENTION

This invention relates to a process of preparing granular porous silicone rubbers having a small specific gravity.

Since silicone rubbers are quite harmless for living bodies, they are used quite extensively as the materials for forming portions of human bodies, for example, materials to be embedded in human bodies and materials to make up lost portions thereof.

However, the prior art articles made of silicone rubbers prepared for these purposes are solid or spongy lumps of large specific gravity so that when they are embedded in human bodies or used to make up lost portions thereof they give different feeling of hardness from that of the human bodies, thus giving the feeding of alien substances.

SUMMARY OF THE INVENTION

It is an object of this invention to provide an improved process for preparing granular porous silicone rubbers having a small specific gravity and especially suitable to prepare articles to be embedded in human bodies or to be used to make up lost portions thereof.

Another object of this invention is to provide porous granules of silicone rubber of a small specific gravity suitable to prepare articles to be embedded in human bodies or to be used to make up lost portions thereof that do not give the feeling of alien substances.

According to this invention these and further objects can be accomplished by providing a process for preparing granular porous silicone rubbers comprising the steps of preparing a composition containing a siloxanediol composition expressed by a formula

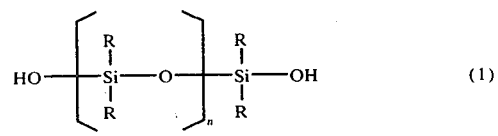

(1)

wherein R respectively represents a methyl radical, a phenyl radical or a vinyl radical and n is an integer of from 500 to 50,000, at least 0.5 % by weight based on the weight of the compound expressed by formula (1) of a siloxanediol hydride compound expressed by a formula

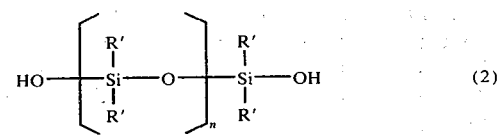

(2)

wherein R' respectively represent a hydrogen radical or a methyl radical but at least one of the R' is a hydrogen radical and n is an integer of from 2 to 1,000, a vulcanization catalyst and an emulsifying agent; dispersing the composition in water and vulcanizing the resulting emulsion while stirring the same.

The composition consisting of the compounds expressed by equations (1) and (2), a vulcanization catalyst and an emulsifying agent is dispersed in water. The dispersion is effected by incorporating the composition into water and then stirring the mixture. Alternatively, the emulsifying agent alone may be dissolved in water and then remaining constituents of the composition are incorporated into the water followed by stirring.

The quantity of the composition expressed by equation (2) is at least 0.5 % by weight based on the quantity of the compound expressed by equation (1), preferably from 0.5 to 5% by weight. Although any suitable quantity of the vulcanization catalyst may be used, a preferred quantity is from about 0.5 to 5% by weight based on the compound expressed by equation (1). Also, although any suitable quantity of the emulsifying catalyst may be used, a preferred quantity is from about 2 to 10 % by weight based on the quantity of the water used. Further, any suitable quantity of the composition may be incorporated into water, but it is advantageous to incorporate 3 to 10% by weight of the composition based on the weight of the water, preferably from 5 to 7 % by weight.

The water may be cold or warm, but warm water at a temperature of about 70° to 95°C is preferred.

Any one or combinations of the following compounds may be used as the compound expressed by equation (1)

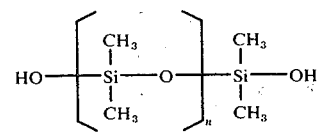

$n = 500 - 50,000$, liquid

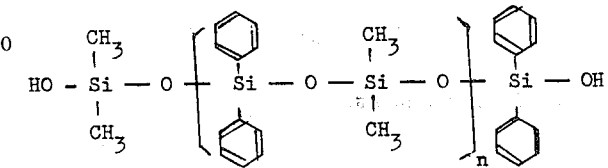

$n = 5,000$, liquid

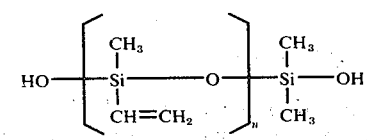

$n = 500 - 50,000$, liquid

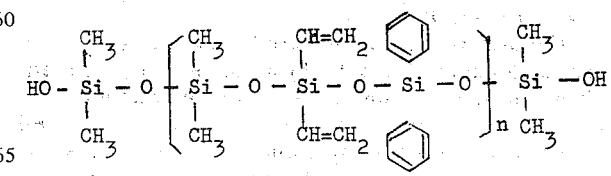

$n = 5,000$, liquid.

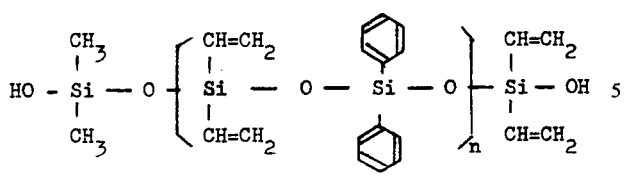

n = 5,000, liquid.

etc.

Further, any one or combinations of the following compounds may be used as the compound expressed by equation (2)

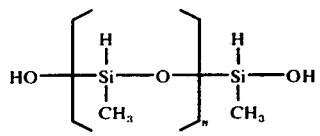

$n = 2 - 1,000$, liquid

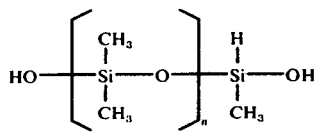

$n = 2 - 1,000$, liquid.

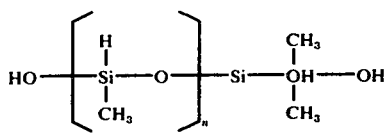

$n = 2 - 1,000$, liquid.

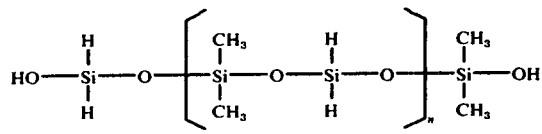

$n = 2 - 1,000$, liquid.

etc.

Tin compounds of higher alcohols, for example dibutyl tin laurate and stannous octoate, are used as the vulcanization catalysts.

As the emulsifying agent may used a synthetic detergent such as sodium benzene sulfonate, and various anioic, cationic and nonionic surface active agents.

Vulcanization Reaction

The dispersed liquid prepared as described above is stirred for about 5 minutes by means of a rotary emulsifying machine to cause a vulcanization reaction.

During the vulcanization reaction, the siloxanediol compound expressed by formula (1) and the siloxanediol hydride compound expressed by formula (2) undergo a condensation reaction wherein the compound of formula (2) releases hydrogen, thus rendering the resulting silicone rubber to be porous. Since the reaction is carried out while stirring, the resulting silicon rubber is granulized. Thus, porous granules of silicone rubber are obtained. The granules are then washed with water and dried to obtain a final product having a particle size of from 0.1 to 1.0 mm and a bulk specific gravity of 0.05 to 0.5.

The granules are suitable for use in orthopedic operations. For example, when mixed with a silicone oil they form unique material suitable for forming artificial breasts. The artificial breast made of this material is light in weight and has a feeling of hardness resembling to that of the human body so that it does not give the feeling of an alien substance. Further, the manner of hanging down of the artificial breast resembles that of the natural one.

Further, as the novel granular porous silicone rubber has suitable cushioning property it is suitable to prepare cushion for preventing bedsores of sick persons. In addition, the novel granules may be used as shock absorbing material in various industrial fields.

To have a better understanding of the invention following examples are given.

EXAMPLE 1

50 g of a siloxanediol compound expressed by formula

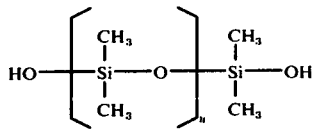

where $n = 10,000$, 0.25 g of a siloxanediol hydride compound expressed by a formula

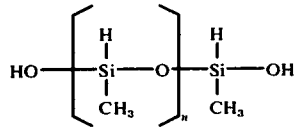

where $n = 100$, and 1.0 g of tin dibutyl laurate were incorporated into 1,000 g of warm water having a temperature of about 80°C and in which 20 g of a synthetic detergent (containing sodium benzenesulfonate as the major ingredient) has been dissolved, and the mixture was stirred in a rotary emulsifying machine to form an emulsion. The emulsion was then stirred for about 5 minutes in a high speed stirrer rotating at a speed of 10,000 to 18,000 r.p.m. for vulcanizing the emulsion. The resulting product was washed with water and dried to obtain discrete fine granules of porous silicone rubber having a particle size of from 0.5 to 0.8 mm and a bulk specific gravity of about 0.25 to 0.27.

The granules thus obtained were admixed with a suitable quantity of a silicone oil having a viscosity of about 3,000 to 5,000 CS, preferably at a ratio of 1 part of the silicone oil to 2 to 3 parts of the granules to prepare a material for forming artificial breasts having a light weight and a feeling of hardness greatly resembling to that of the human body so that not giving a feeling of aligne substances. Further, these artificial breasts depend just like the human breasts.

EXAMPLE 2

In the same manner as in Example 1, 60 g of a siloxanediol compound expressed by a general formula

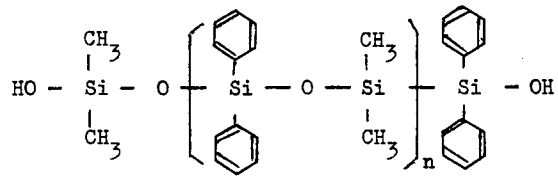

wherein $n = 5,000$, 1.8 g of a siloxanediol hydride compound expressed by a formula

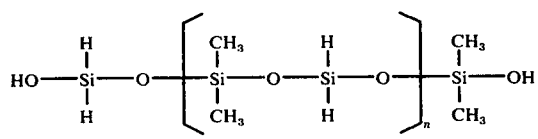

where $n = 100$, and 1.2 g of tin octoate were dispersed in water and the resulting emulsion was vulcanized to obtain discrete granules of porous silicone rubber having a particle size of about 0.5 to 0.6 mm and a bulk specific gravity of from about 0.20 to 0.25.

The resulting granules were found to be most suitable to prepare cushions for preventing bedsores of sick persons.

EXAMPLE 3

In the same manner as in Example 1, 60 g of a siloxanediol compound expressed by a formula

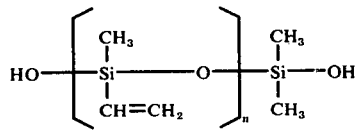

where $n = 5,000$, 3.0 g of a siloxanediol hydride compound expressed by a formula

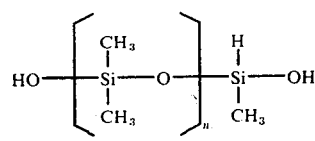

wherein $n = 100$, and 1.2 g of tin butyl laurate were dispersed in water and the resulting emulsion was vulcanized to obtain granules of porous silicone rubber having a particle size of about 0.5 to 0.6 mm and a bulk specific density of about 0.15 to 0.20.

The resulting granules were used to prepare artificial breasts in the same manner as in Example 1 with satisfactory result.

I claim:

1. A process for preparing granular porous silicone rubbers comprising the steps of preparing a composition containing a siloxanediol composition expressed by a formula

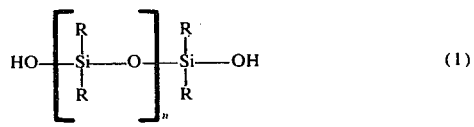

wherein R respectively represents a methyl radical, a phenyl radical or a vinyl radical and n is an integer of from 500 to 50,000, from 0.5 to 5% by weight based on the weight of the compound expressed by formula (1) of a siloxanediol hydride compound expressed by a formula

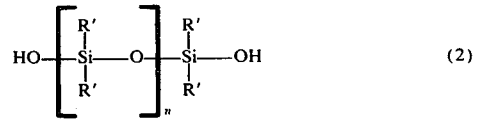

wherein R' respectively represents a hydrogen radical or a methyl radical but at least one of the R' radicals is a hydrogen radical, and n is an integer of from 2 to 1,000, a vulcanization catalyst, and an emulsifying agent, dispersing from 3 to 10% by weight of said composition in water based on the weight of the water, the amount of said emulsifying agent being 2 to 10% by weight based on the weight of said water, and vulcanizing the resulting emulsion while stirring same.

2. The process according to claim 1, wherein said vulcanization catalyst is used by 0.5 to 5% by weight based on the weight of the compound of formula (1).

3. The process according to claim 1, wherein said water is maintained at a temperature of from 70° to 95°C.

4. The process according to claim 1, wherein said composition further contains a surface active agent.

5. The porous silicone rubber granule prepared according to the process of claim 1.

6. The porous silicone rubber granule as defined in claim 5, wherein said granule has a particle size of from about 0.1 mm to about 1.0 mm and a bulk specific gravity of from about 0.05 to about 0.5.

* * * * *